United States Patent [19]

Delgado

[11] 4,321,216

[45] Mar. 23, 1982

[54] POLAR-NONPOLAR SOLVENT SYSTEM FOR DEOILING HYDROCARBON SULFONATES

[75] Inventor: Emil Delgado, La Grange, Ga.

[73] Assignee: Phillips Petroleum Company, Bartlesville, Okla.

[21] Appl. No.: 114,447

[22] Filed: Jan. 22, 1980

[51] Int. Cl.$^3$ ............................................. C07C 139/00
[52] U.S. Cl. ............................. 260/504 S; 260/505 P; 260/504 R
[58] Field of Search ............. 260/505 P, 504 S, 504 R

[56] References Cited

U.S. PATENT DOCUMENTS

| | | | |
|---|---|---|---|
| 2,655,530 | 10/1953 | Nevison | 260/505 P |
| 2,673,208 | 3/1954 | Andrews | 260/505 |
| 2,820,056 | 1/1958 | Gerhart et al. | 260/505 P |
| 2,880,173 | 3/1959 | Honeycutt | 260/505 |

*Primary Examiner*—Alan Siegel

[57] ABSTRACT

Hydrocarbon sulfonates, e.g., petroleum sulfonates, are separated from unsulfonated hydrocarbon e.g., petroleum hydrocarbon oil, by employing a mixture or solvent system comprising an immiscible polar and a nonpolar component. Preferably the immiscible polar component is a carboxylic acid having from 1 to about 4 carbon atoms e.g., formic acid, and the nonpolar hydrocarbon is one containing 3 to about 12 carbon atoms and can be at least one of an alkane, cycloalkane, aromatic and akylated aromatic, an alkene, or a cycloalkene. A petroleum sulfonate is separated from unsulfonated petroleum oil employing a mixture of formic acid and n-octane.

4 Claims, No Drawings

POLAR-NONPOLAR SOLVENT SYSTEM FOR DEOILING HYDROCARBON SULFONATES

BRIEF SUMMARY OF THE INVENTION

A solvent system comprising immiscible polar and nonpolar components, e.g., a carboxylic acid, such as formic acid and a hydrocarbon, e.g., octane, is employed to effect separation of a hydrocarbon sulfonate, e.g., petroleum sulfonate, from unsulfonated oil in a mixture obtained upon preparation of such sulfonates.

DETAILED DESCRIPTION

This invention relates to the recovery of a hydrocarbon sulfonate, e.g., petroleum sulfonate, from a mixture of it and unsulfonated hydrocarbon, e.g., a hydrocarbon or petroleum oil. In one of its aspects the invention relates to the provision of a solvent system for the separation.

In one of its concepts, the invention provides a process for the separation of a hydrocarbon sulfonate, e.g., petroleum sulfonate, from a mixture of it and unsulfonated hydrocarbon, e.g., unsulfonated hydrocarbon oil, by contacting the mixture with a solvent system comprising an immiscible polar component and a nonpolar component.

The production of hydrocarbon sulfonates or petroleum sulfonates and their uses are well known.

The recovery of, say, a petroleum sulfonate from unsulfonated oil, particularly in these times of energy problems, can be accomplished in an improved manner by use of my invention.

For example, I have found that carboxylic acids having from 1 to about 4 carbon atoms, e.g., formic, acetic, propionic, and butyric acids, are suitable for use with nonpolar hydrocarbon components containing 3 to about 12 carbon atoms, for example, alkanes such as propane, butane, pentane, hexane, heptane, octane, nonane, decane, dodecane, and the like; cycloalkanes such as cyclopentane and cyclohexane; aromatic and alkylated aromatic compounds such as benzene, toluene, ethylbenzene, xylenes and the like. Further as nonpolar component selected alkenes and cycloalkenes, e.g., hexenes, octenes, decenes and the like as well as cyclopentene and cyclohexene are also useful.

It is an object of this invention to provide a process for the recovery of a hydrocarbon sulfonate, e.g., petroleum sulfonate, from a mixture of it and unsulfonated hydrocarbon. It is another object of this invention to provide a solvent system for the improved recovery of a hydrocarbon sulfonate from unsulfonated hydrocarbon.

Other aspects, concepts, objects, and several advantages of the invention are apparent from a study of this disclosure and the appended claims.

According to the present invention, there is provided a process for the recovery of a hydrocarbon sulfonate from unsulfonated hydrocarbon which comprises treating such a mixture under conditions suitable for separation into its components with a solvent system comprising an immiscible polar and nonpolar component.

More specifically, according to the invention, carboxylic acids as herein described, are combined in a solvent system with nonpolar hydrocarbon components, also as herein described, for separating from mixtures, as herein described, hydrocarbon sulfonates or petroleum sulfonates from unsulfonated hydrocarbon or oil.

Thus, in accordance with the present invention, solvent systems comprising immiscible polar and nonpolar components such as, respectively, carboxylic acid, e.g., formic acid, and hydrocarbon such as octane effect the separation of mixtures comprising petroleum sulfonates and unsulfonated oil into the respective components. The petroleum sulfonates and inorganic salt impurities are concentrated in the polar phase whereas the unsulfonated oil is concentrated in the nonpolar phase. It is contemplated that the invention process is generally applicable to the separation of mixtures comprising unsulfonated oil and petroleum sulfonates regardless of the origin of said mixtures, e.g., the instant process can be used with commercially available petroleum sulfonates comprising said sulfonates, unsulfonated oil, inorganic salts and water as well as similar mixtures obtained from conventional or experimental sulfonation procedures e.g., such as the $SO_3$ sulfonation of sulfonatable hydrocarbon feedstocks in diluents such as methylene chloride.

One skilled in the art with possession of this disclosure, having studied the same, will recognize that other polar components can be determined by testing, taking such component and the respective nonpolar component into such testing.

Other polar components can be determined by testing, taking such component and the respective nonpolar component into such testing. Admixtures of water and carboxylic acids are also suitable for use as the polar component in the present process. Broadly, the carboxylic acid component can contain up to 60 weight percent water with a preferred range of 10 to 30 weight percent water. Commercially available formic acid containing 88 weight percent formic acid and 12 weight percent water is preferred as the polar component in the inventive solvent system.

In general, the process is carried out at ambient temperature at which the solvent system is essentially immiscible. It is contemplated that the instant process can be practiced at higher temperatures even though the system essentially assumes a state of miscibility provided that said system reverts to an immiscible state on cooling to ambient conditions. It is contemplated that chilling, e.g., to 0° C., will in some cases facilitate complete separation of the polar and nonpolar phases. In any case, the petroleum sulfonate components and inorganic salts become concentrated ultimately in the polar phase and the unsulfonated oil becomes concentrated in the nonpolar phase.

Petroleum sulfonates of increasing equivalent weight become progressively more soluble in the nonpolar component of the inventive system and therefore, in a given separation for such materials, the selection of a lower molecular weight member of the suitable carboxylic acids with a lower molecular weight member of the hydrocarbon moiety can minimize losses of petroleum sulfonate to the nonpolar phase.

Back extraction of the separated nonpolar phase, e.g., n-octane with fresh portions of the polar phase, e.g., aqueous formic acid can likewise minimize losses of petroleum sulfonates to the nonpolar phase.

The relative amounts of materials to be used can be readily determined. The following ranges are suitable:

| Parameter | Broad | Preferred | Most Preferred |
|---|---|---|---|
| Total Initial Solvent Volume, mL | 1:1 to 100:1 | 5:1 to 60:1 | 10:1 to 40:1 |
| Wt, g, of Crude Sample Carboxylic Acid Volume | 1:10 to 10:1 | 1:5 to 5:1 | 1:2 to 2:1 |
| Hydrocarbon Volume | | | |

EXAMPLE

A 10 g sample of Witco Chemical Co. TRS-16 petroleum sulfonates was dissolved in 100 mL of aqueous formic acid (12 weight percent $H_2O$) and placed in a 250 mL separatory funnel with 100 mL of n-octane. The contents of the separatory funnel were shaken and then allowed to stand for phase separation. The n-octane phase was removed and the polar sulfonate-containing formic acid phase was extracted two more times with additional 100 ml portions of n-octane. Each of the octane extracts was individually back-extracted with 100 ml portions of formic acid to give a final total volume of 300 ml octane and 300 ml formic acid.

The combined formic acid extracts were concentrated by heat lamp in a well-ventilated hood and then dried to constant weight in a vacuum oven. The final weight of the sample was 6.21 g corresponding to ca. 62.1 weight percent petroleum sulfonate based on the initial 10 g sample of TRS-16. This value is in excellent agreement with the typical analysis for TRS-16 provided by Witco Chemical Co., viz., 62% active petroleum sulfonate, 33% unreacted oil, 4.5% water and 0.5% inorganic salts.

The TRS-16 sample was further characterized by elution column chromatography (ASTM D2548) to give a value of 62.1% active petroleum sulfonates which is in good agreement with both the value provided by Witco and the results obtained on using the present inventive procedure.

Reasonable variation and modification are possible within the scope of the foregoing disclosure and the appended claims to the invention the essence of which is that a two-phase solvent system comprising an immiscible polar and a nonpolar component has been set forth and used in a process for recovering from a mixture, containing the same, a hydrocarbon sulfonate from unsulfonated hydrocarbon, as described.

I claim:

1. A process for the separation from a mixture containing the same of a hydrocarbon sulfonate and unsulfonated hydrocarbon which comprises contacting said mixture under phase-forming conditions with an immiscible solvent system comprising an immiscible polar component and a nonpolar component and recovering in said carboxylic acid component hydrocarbon sulfonate substantially freed from unsulfonated hydrocarbon.

2. A process according to claim 1 wherein the immiscible polar solvent is at least one selected from carboxylic acids containing from 1 to about 4 carbon atoms and the nonpolar component is a hydrocarbon containing from 3 to about 12 carbon atoms and is selected from alkanes, aromatic and alkylated aromatic compounds, and alkenes and cycloalkenes; the components being so selected that under the conditions of contacting the two phases will be formed.

3. A process according to claim 1 wherein the polar component is at least one selected from formic, acetic, propionic and butyric acids and the nonpolar component is at least one selected from propane, butane, pentane, hexane, heptane, octane, nonane, decane, dodecane, cyclopentane, cyclohexane, benzene, toluene, ethylbenzene, xylenes, hexenes, octenes, decenes, cyclopentene, and cyclohexene.

4. A process according to claim 1 wherein petroleum sulfonate is separated from unsulfonated or unreacted oil employing a solvent system comprising formic acid and n-octane.

* * * * *